United States Patent
Herrera et al.

(10) Patent No.: US 11,839,535 B2
(45) Date of Patent: *Dec. 12, 2023

(54) BLADDER MANAGEMENT SYSTEMS

(71) Applicant: Spinal Singularity, Inc., San Clemente, CA (US)

(72) Inventors: Derek Herrera, San Clemente, CA (US); Alex Shen, Berkeley, CA (US)

(73) Assignee: Spinal Singularity, Inc., San Clemente, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/896,105

(22) Filed: Jun. 8, 2020

(65) Prior Publication Data
US 2020/0375714 A1    Dec. 3, 2020

Related U.S. Application Data

(60) Division of application No. 15/877,228, filed on Jan. 22, 2018, now Pat. No. 10,675,134, which is a
(Continued)

(51) Int. Cl.
*A61F 2/00* (2006.01)
*A61F 2/48* (2006.01)

(52) U.S. Cl.
CPC ......... *A61F 2/0027* (2013.01); *A61F 2/0022* (2013.01); *A61F 2/48* (2021.08);
(Continued)

(58) Field of Classification Search
CPC ......... A61F 2/0022–0027; A61F 2/042; A61F 2002/047
See application file for complete search history.

(56) References Cited

U.S. PATENT DOCUMENTS 3,630,206 A    12/1971    Gingold
3,812,841 A    5/1974    Isaacson
(Continued)

FOREIGN PATENT DOCUMENTS

EP    1096900    9/2005
EP    2094343    10/2017
(Continued)

OTHER PUBLICATIONS

USPTO; Non-Final Office Action dated Jan. 19, 2021 in the U.S. Appl. No. 15/785,403.
(Continued)

*Primary Examiner* — Thaddeus B Cox
(74) *Attorney, Agent, or Firm* — SNELL & WILMER L.L.P.

(57) ABSTRACT

The disclosure relates generally to an extended use systems and devices for management of bladder function for people with urinary dysfunction. The system includes a catheter which can include a sensor that can determine bladder condition and a valve that can control fluid flow. The catheter can be placed inside the bladder using devices that facilitate insertion and extraction. The placement of the catheter can be done by a trained individual such as a patient, as well as a clinician, a nurse, or a caretaker. Once placed inside the bladder, the catheter can be fully-internal, meaning no portion of the catheter is visible from outside of the patient's body.

17 Claims, 9 Drawing Sheets

Related U.S. Application Data continuation of application No. 15/721,096, filed on Sep. 29, 2017, now Pat. No. 10,743,975, which is a division of application No. 15/419,948, filed on Jan. 30, 2017, now Pat. No. 9,775,698, which is a continuation-in-part of application No. PCT/US2016/014648, filed on Jan. 23, 2016.

(60) Provisional application No. 62/107,203, filed on Jan. 23, 2015.

(52) U.S. Cl.
CPC . *A61F 2210/009* (2013.01); *A61F 2220/0033* (2013.01); *A61F 2250/0002* (2013.01); *A61F 2250/0003* (2013.01); *A61F 2250/0013* (2013.01)

(56) References Cited

U.S. PATENT DOCUMENTS

| | | |
|---|---|---|
| 3,938,529 A | 2/1976 | Gubbons |
| 4,043,346 A | 8/1977 | Mobley |
| 4,168,699 A | 9/1979 | Hauser |
| 4,710,169 A | 12/1987 | Christopher |
| 4,932,938 A | 6/1990 | Goldberg |
| 4,986,810 A | 1/1991 | Semrad |
| 5,041,092 A | 8/1991 | Barwick |
| 5,140,999 A | 8/1992 | Ardito |
| 5,366,506 A | 11/1994 | Davis |
| 5,380,268 A | 1/1995 | Wheeler |
| 5,411,507 A | 5/1995 | Heckele |
| 5,476,434 A | 12/1995 | Kalb et al. |
| 5,628,770 A | 5/1997 | Thome et al. |
| 5,713,877 A | 2/1998 | Davis |
| 5,749,826 A | 5/1998 | Faulkner |
| 6,053,897 A | 4/2000 | Sachse |
| 6,066,088 A | 5/2000 | Davis |
| 6,132,365 A | 10/2000 | Sigurdsson |
| 6,167,886 B1 * | 1/2001 | Engel .................. A61F 2/0027 128/885 |
| 6,527,702 B2 | 3/2003 | Whalen |
| 6,565,536 B1 | 5/2003 | Sohn |
| 6,602,243 B2 | 8/2003 | Noda |
| 6,638,208 B1 | 10/2003 | Natarajan et al. |
| 6,835,183 B2 | 12/2004 | Lennox et al. |
| 7,001,327 B2 | 2/2006 | Whalen |
| 7,147,606 B1 | 12/2006 | Chang et al. |
| 7,338,028 B2 | 3/2008 | Zimmerling et al. |
| 7,415,308 B2 | 8/2008 | Gerber et al. |
| 7,803,106 B2 | 9/2010 | Whalen et al. |
| 8,801,697 B2 | 8/2014 | Yugari |
| 8,882,652 B2 | 11/2014 | Vitzthum |
| 9,011,314 B2 | 4/2015 | Davis et al. |
| 9,452,278 B2 | 9/2016 | Davis et al. |
| 9,775,698 B2 | 10/2017 | Herrera et al. |
| 10,675,134 B2 | 6/2020 | Herrera |
| 10,675,435 B2 | 8/2020 | Herrera |
| 10,751,506 B2 | 8/2020 | Herrera |
| 2002/0010476 A1 | 1/2002 | Mulholland |
| 2002/0107540 A1 | 8/2002 | Walen |
| 2002/0143292 A1 | 10/2002 | Flinchbaugh |
| 2002/0165427 A1 | 11/2002 | Yachia et al. |
| 2002/0198506 A1 | 12/2002 | Whalen |
| 2003/0153873 A1 | 8/2003 | Luther et al. |
| 2003/0167069 A1 | 9/2003 | Gonzales |
| 2003/0229263 A1 | 12/2003 | Connors et al. |
| 2004/0019369 A1 | 1/2004 | Duncan et al. |
| 2004/0106899 A1 | 6/2004 | McMichael et al. |
| 2005/0054995 A1 * | 3/2005 | Barzell ............... A61M 3/0229 604/317 |
| 2005/0177102 A1 | 8/2005 | Hart |
| 2005/0216069 A1 | 9/2005 | Cohen et al. |
| 2006/0020297 A1 | 1/2006 | Gerber |
| 2006/0184090 A1 | 8/2006 | Davis et al. |
| 2006/0211946 A1 | 9/2006 | Mange et al. |
| 2006/0247723 A1 | 11/2006 | Gerber et al. |
| 2008/0269546 A1 | 10/2008 | Wilkie et al. |
| 2008/0294069 A1 | 11/2008 | Stickler et al. |
| 2009/0157053 A1 | 6/2009 | Davis et al. |
| 2010/0234876 A1 | 9/2010 | Watson |
| 2010/0312225 A1 | 12/2010 | Armistead |
| 2010/0331825 A1 | 12/2010 | Hakky |
| 2011/0054404 A1 | 3/2011 | Tanabe et al. |
| 2011/0066139 A1 | 3/2011 | Winegar |
| 2012/0316584 A1 | 12/2012 | Miles |
| 2013/0041430 A1 | 2/2013 | Wang et al. |
| 2013/0090630 A1 | 4/2013 | Winegar |
| 2013/0231639 A1 | 9/2013 | Tatlow |
| 2014/0148648 A1 | 5/2014 | Tycast et al. |
| 2014/0213979 A1 | 7/2014 | Boyco et al. |
| 2014/0214009 A1 | 7/2014 | Reyes |
| 2014/0371803 A1 | 12/2014 | Grill et al. |
| 2015/0087896 A1 | 3/2015 | Wei et al. |
| 2015/0250991 A1 | 9/2015 | Silvestro |
| 2015/0366462 A1 | 12/2015 | Ramos et al. |
| 2016/0000641 A1 | 1/2016 | Driscoll et al. |
| 2016/0279389 A1 | 9/2016 | Rosenberg |
| 2016/0287847 A1 | 10/2016 | Herrera |
| 2017/0079761 A1 * | 3/2017 | Connors ................ A61B 5/205 |
| 2017/0156838 A1 | 6/2017 | Herrera |
| 2018/0036107 A1 | 2/2018 | Herrera |
| 2018/0140799 A1 | 5/2018 | Herrera |
| 2018/0153669 A1 | 6/2018 | Herrera |
| 2018/0153670 A1 | 6/2018 | Herrera |
| 2018/0153671 A1 | 6/2018 | Herrera |
| 2018/0264226 A1 | 9/2018 | Erbey |
| 2020/0384241 A1 | 12/2020 | Herrera |
| 2020/0406004 A1 | 12/2020 | Herrera |
| 2021/0121097 A1 | 4/2021 | Herrera |
| 2021/0267740 A1 | 9/2021 | Herrera |
| 2023/0001155 A1 | 1/2023 | Herrera |

FOREIGN PATENT DOCUMENTS

| | | |
|---|---|---|
| EP | 3247309 | 11/2017 |
| WO | 2000002499 | 1/2000 |
| WO | 2001010358 | 2/2001 |
| WO | 2011032150 | 3/2011 |
| WO | 2016118943 | 7/2016 |
| WO | 2017015351 | 1/2017 |
| WO | 2017172998 | 10/2017 |
| WO | 2018200643 | 11/2018 |
| WO | 2019068104 | 4/2019 |

OTHER PUBLICATIONS

USPTO; Non-Final Office Action dated Jan. 8, 2021 in the U.S. Appl. No. 15/785,405.
USPTO; Notice of Allowance dated Apr. 15, 2021 in the U.S. Appl. No. 15/785,405.
PCT; International Search Report and Written Opinion in the PCT Application No. PCT/US2020/057429 dated Feb. 11, 2021.
USPTO; Notice of Allowance dated Aug. 17, 2017 in U.S. Appl. No. 15/419,948.
USPTO; Final Office Action dated Jul. 13, 2017 in U.S. Appl. No. 15/419,948.
USPTO; Office Action dated Jun. 16, 2017 in U.S. Appl. No. 15/419,948.
USPTO; Restriction Requirement dated Mar. 23, 2017 in U.S. Appl. No. 15/419,948.
USPTO; Restriction Requirement dated Jul. 5, 2018 in U.S. Appl. No. 15/072,345.
USPTO; Non-Final Office Action dated Oct. 23, 2018 in U.S. Appl. No. 15/072,345.
USPTO; Final Office Action dated Mar. 25, 2019 in U.S. Appl. No. 15/072,345.
USPTO; Non-Final Office Action dated Aug. 26, 2019 in U.S. Appl. No. 15/877,228.
USPTO; Non-Final Office Action dated Sep. 12, 2019 in U.S. Appl. No. 15/785,405.

(56) References Cited

OTHER PUBLICATIONS

USPTO; Non-Final Office Action dated Sep. 13, 2019 in U.S. Appl. No. 15/072,345.
USPTO; Non-Final Office Action dated Sep. 13, 2019 in U.S. Appl. No. 15/785,403.
USPTO; Restriction Requirement dated Aug. 2, 2019 in the Appl. No. 15/721,096.
USPTO; Restriction Requirment dated Aug. 9, 2019 in the U.S. Appl. No. 15/877,228.
USPTO; Final Office Action dated Dec. 6, 2019 in the U.S. Appl. No. 15/877,228.
USPTO; Final Office Action dated Jan. 22, 2020 in the U.S. Appl. No. 15/721,096.
USPTO; Final Office Action dated Jan. 30, 2020 in the U.S. Appl. No. 15/785,403.
USPTO; Notice of Allowance dated Feb. 5, 2020 in the U.S. Appl. No. 15/072,345.
USPTO; Final Office Action dated Feb. 12, 2020 in the U.S. Appl. No. 15/785,405.
USPTO; Non-Final Office Action dated Apr. 13, 2020 in U.S. Appl. No. 15/785,398.
USPTO; Notice of Allowance dated Apr. 23, 2020 in the U.S. Appl. No. 15/877,228.
USPTO; Notice of Allowance dated Apr. 24, 2020 in the U.S. Appl. No. 15/785,398.
USPTO; Non-Final Office Action dated Jun. 4, 2020 in the U.S. Appl. No. 15/785,403.
USPTO; Final Office Action dated Oct. 9, 2020 in the U.S. Appl. No. 15/785,403.
USPTO; Non-Final Office Action dated Jun. 2, 2020 in the U.S. Appl. No. 15/785,405.
USPTO; Final Office Action dated Sep. 16, 2020 in the U.S. Appl. No. 15/785,405.
EPO; Extended Search Report and Written Opinion dated Jan. 2, 2018 in EP16740891.3.
EPO; Supplementary European Search Report dated Jan. 19, 2018 in EP16740891.3.
Mexico: Non-Final Office Action dated Jan. 26, 2018 in MX2017-009517.
AUIPO; Office Action dated Jul. 22, 2019 in Australian Application No. 2016209038.
UK; Office Action dated Feb. 5, 2020 in UK. Application No. GB1713519.3.
EP; First Office Action in the EP Application No. 16740891.3 dated Feb. 10, 2020.
GB; Examination Report in the GB Application No. GB1713519.5 dated Sep. 17, 2020.
AU; Examination Report No. 1 in the AU Application No, 2016209038 dated Jul. 22, 2019.
AU; Examination Report No. 2 in the AU Application No. 2016209038 dated Jul. 10, 2020.
AU; Notice of Allowance in the AU Application No. 2016209038 dated Jul. 21, 2020.
EP; Notice to Respond to Search in the EP Application No. 18792715.7 dated May 8, 2020.
EP; Supplemental Search Report in the EP Application No. 16740891.3 dated Dec. 18, 2017.
GB; First Examination Report in the GB Application No. GB1713519.5 dated Jun. 5, 2020.
GB; Second Examination Report in the GB Application No. GB1713519.5 dated Nov. 17, 2020.
IL; First Exam Report in the IL Application No. 005164IL dated Aug. 5, 2020.
PCT; International Search Report dated Jul. 28, 2016 in International Application No. PCT/US2016/014648.
PCT; International Preliminary Report on Patentability dated Jul. 25, 2017 in International Application No. PCT/US2016/014648.
PCT; Written Opinion dated Jul. 25, 2016 in International Application No. PCT/US2016/014648.
PCT; International Search Report dated Aug. 17, 2017 in International Application No. PCT/US2017/024862.
PCT; Written Opinion dated Aug. 17, 2017 in International Application No. PCT/US2017/024862.
PCT; International Preliminary Report on Patentability dated Oct. 2, 2018 in International Application. No. PCT/US2017/024862.
PCT; International Search Report dated PCT/US2018/053806 dated Jan. 28, 2019 in International Application No. PCT/US2018/053806.
PCT; Written Opinion dated Jan. 28, 2019 in International Application No. PCT/US2018/053806.
PCT; Written Opinion dated Aug. 17, 2017 in the PCT Application No. PCT/US2017/024862.
PCT; International Search Report and Written Opinion in the PCT Application No. PCT/US2018/053806 dated Jan. 18, 2018.
PCT; International Search Report and Written Opinion in the PCT Application No. PCT/US2020/036859 dated Oct. 9, 2020.

\* cited by examiner

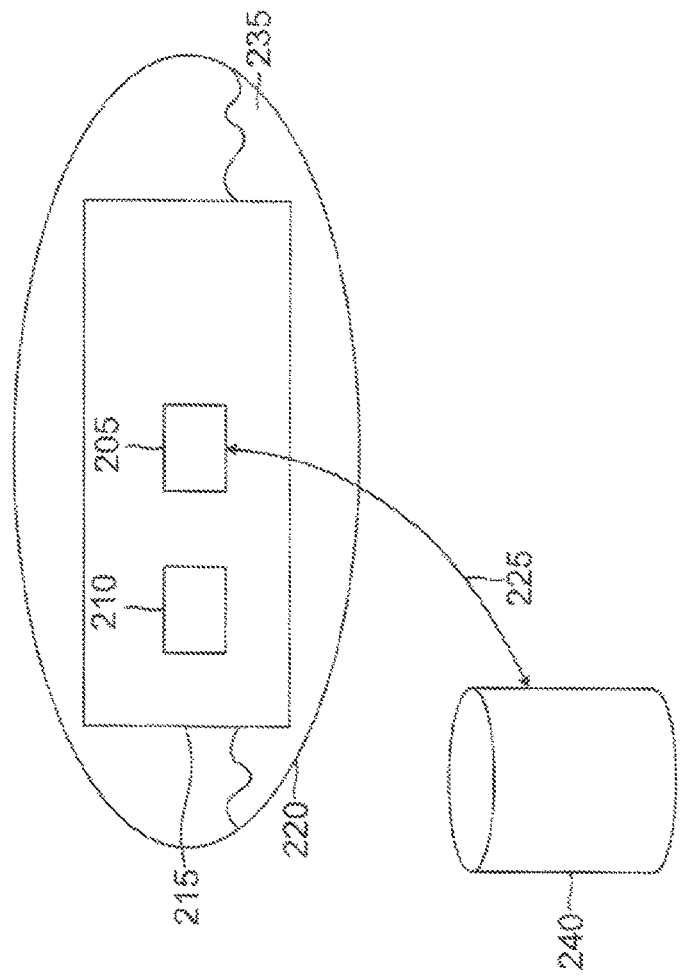
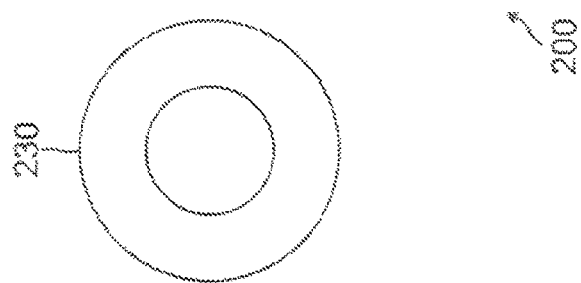
FIG. 2

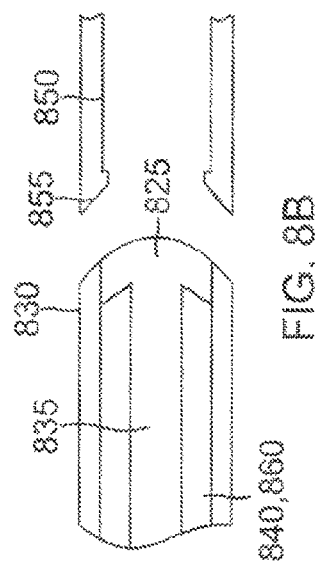
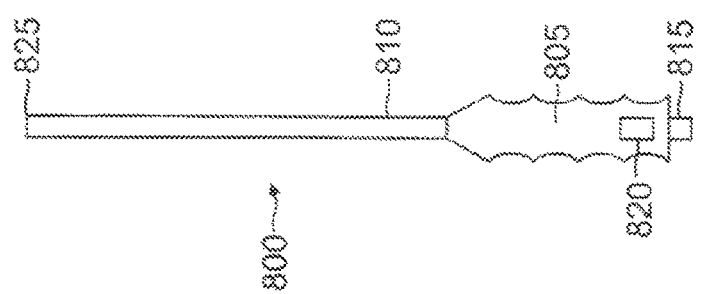

BLADDER MANAGEMENT SYSTEMS

CROSS REFERENCE TO RELATED APPLICATIONS

This application is a divisional of and claims priority to U.S. application Ser. No. 15/877,228 filed Jan. 22, 2018 know U.S. Pat. No. 10,675,134), which is a continuation of and claims priority to U.S. patent application Ser. No. 15/721,096 (now U.S. Pat. No. 10,743,975), filed Sep. 29, 2017, which is divisional of and claims priority to U.S. patent application Ser. No. 15/419,948 (now U.S. Pat. No. 9,775,698), filed Jan. 30, 2017, which is a continuation-in-part of, and claims priority to PCT Patent Application Serial No. PCT/US2016/014648, filed Jan. 23, 2016, which claims benefit to and priority to U.S. Provisional Application Ser. No. 62/107,203, filed Jan. 23, 2015, U.S. Provisional Application Ser. No. 62/279,485, filed Jan. 15, 2016, U.S. Provisional Application Ser. No. 62/275,671, filed Jan. 6, 2016, U.S. Provisional Application Ser. No. 62/231,854, filed Jul. 16, 2015, and U.S. Provisional Application Ser. No. 62/141,520, filed Apr. 1, 2015. Each of the foregoing applications are incorporated herein by reference in their entirety for all purposes.

FIELD

This disclosure generally relates to bladder management systems, and in particular, wireless sensors and urinary catheters.

BACKGROUND

Currently, there are a significant amount of people that suffer from bladder issues where they are unable to sense the amount of urine in their bladder and when they need to urinate. One condition resulting in this symptom is the Neurogenic Bladder, often found in individuals suffering from paralysis. Many of these individuals lack sensation below their levels of injury and this results in someone who is required to use intermittent catheters to allow urine to empty their bladder. Because they are unable to determine the exact amount of urine stored in their bladder, and unable to sense the fullness, they often utilize a time schedule to ensure they don't experience urinary accidents. This is very inefficient and increases the risk of Urinary Tract Infections, urethral damage due to False Passage, and other issues. If these individuals were able to decrease the number of times they are catheterized, it would improve the individual's comfort and decrease their risk of infection and other complications. A device that alerts them the amount of urine currently in their bladder can allow individuals to more accurately determine the timing to release the urine stored in their bladder instead of being required to utilize a time schedule. A valve device that is fully internal to the individual's body, which also allows the individual to open and close the valve from outside the body, would decrease the need to remove and replace the catheter while reducing the likelihood of foreign objects entering the urethra. It is, therefore, desirable to provide an improved sensor and valve on a catheter, that overcomes most, if not all, of the preceding problems.

SUMMARY

The present technology relates to systems and method for controlling the urinary system and, in particular, long-term use device for bladder management and awareness regarding bladder fullness.

BRIEF DESCRIPTION OF THE DRAWINGS

The following drawings and the associated descriptions are provided to illustrate the present disclosure and do not limit the scope of the claims.

FIG. 2 shows a generalized schematic drawing of a sample bladder management system using a signal generating sensor.

FIG. 8A shows a schematic drawing of an embodiment of an insertion device and the catheter.

FIG. 8B shows a schematic drawing of an embodiment of a mating lip of the insertion device of FIG. 8A.

DETAILED DESCRIPTION

Disclosed herein are embodiments of systems that can be used for bladder management, specifically bladder management for Neurogenic Bladder in a patient. For example, embodiments of the system can be used to sense metrics that can be used to determine the amount of urine inside a person's, or an animal's, bladders and/or the pressure of urine in the bladder. However, the disclosed systems can be used for fluid flow control and sensing for other bodily organs as well, and the particular bodily organ described is not limiting. Further, the bladder management can be based on, for example, characteristics of the urine such as pH level, quantity, volume, pressure, urine constituents, color, odor, turbidity, density, possible pathogens, etc. Bladder management can also be based on the dimension of the urethra such as circumference or diameter, pressure of urine inside the bladder, so forth and the particular example used for bladder management are not limiting. As used herein, the term "user" is intended to include any person trained and able to perform the procedure, including the patient, doctor, caregiver, nurse, etc. The term "patient" and "individual" are intended to be interchangeable. The term "body" used herein is defined as "an animate body" including human, animal, and the like.

Bladder Management System

Figure 1:
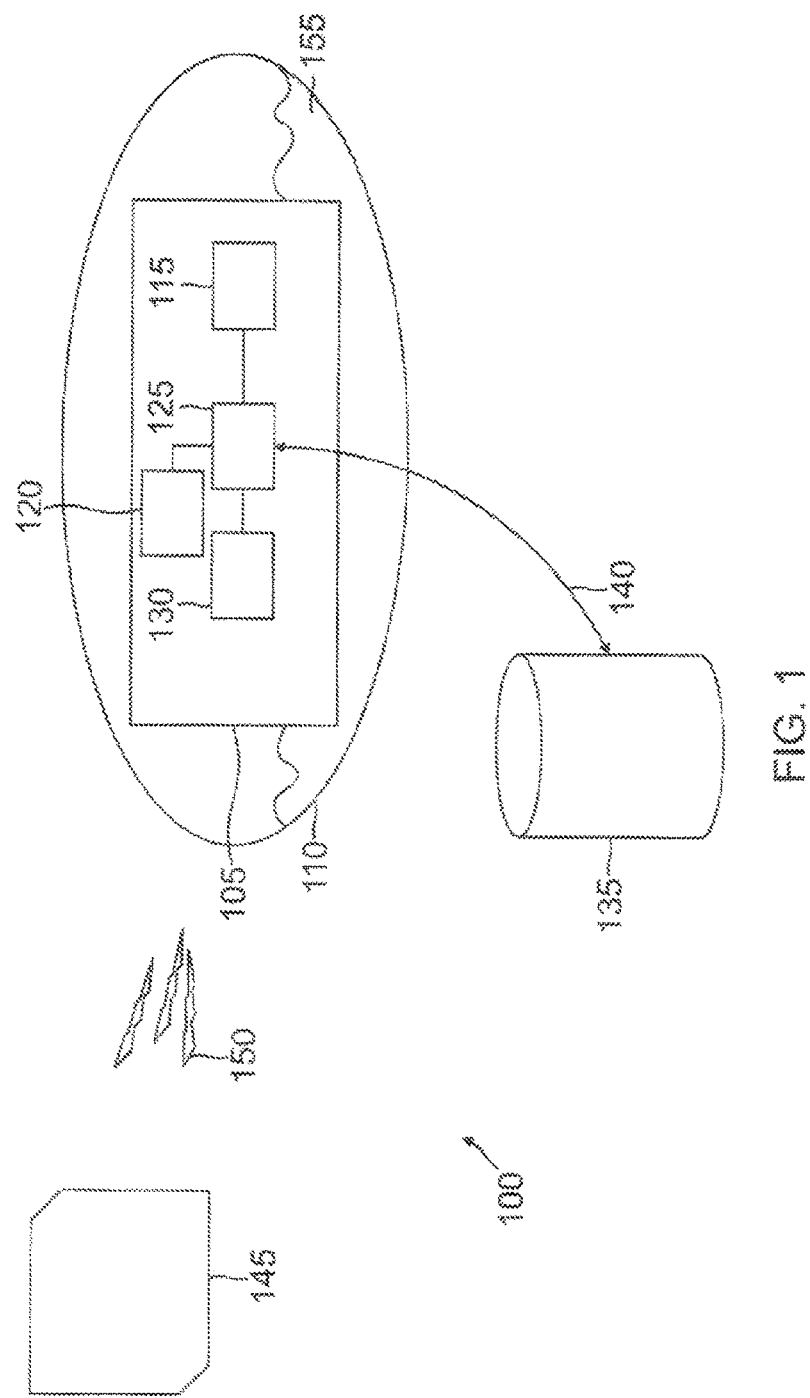
FIG. 1 shows a generalized schematic drawing of a sample bladder management system.

FIG. 1 shows a generalized schematic drawing of a sample bladder management system. A bladder management system 100 can comprise a body. The body can be a long-term use catheter 105. The catheter 105 can be shaped and sized to be introduced into the bladder 110 of a patient. The catheter 105 can be fully-internal to the body of the patient. The catheter 105 can comprise a sensor 115 and a valve 120. The catheter 105 can further comprise a processor 125 and a power source 130. In some embodiments, the bladder management system 100 can comprise a computing device 135, and the processor 125 can be configured to communicate with the computing device 135. For example, the processor 125 can communicate with the computing device using wireless transmission 140. The computing device 135 can be a mobile phone. In some embodiments, the bladder management system 100 can comprise an external powering system 145. The external powering system 145 can be configured to transmit energy to the catheter 105. For example, the power source 130 can be a battery or capacitor, and the external powering system 145 can charge the power source 130 through inductive or wireless means. The external powering system 145 may also utilize energy in other bands of the spectrum (SONAR, Acoustic, Ultrasound, RF, etc) to transmit data that the external unit can sense to extrapolate information about the condition, volume, pressure, or other characteristics of urine in the bladder and also overall bladder health.

The sensor 115 can be used to measure the level of urine 155 in the bladder 110. The sensor 115 can be placed along the body of the catheter 105. The sensor 115 can be inductively and capacitively coupled to the processor 125. The processor 125 can be configured to receive an input from the sensor 115 and produce an output that can be used for bladder management. For example, the processor 125 can receive data from the sensor 115, and the output from the processor 125 can be used to alert the user about the characteristics of urine and bladder. This external system may also be used to open or close the valve 120. The valve 120 can be in a fluid communication with the catheter 105. The valve 120 can be configured to restrict or allow flow of fluid from within the bladder 110. For example, the valve 120 can be positioned within a portion of the catheter 105 along the urethra. The power source 130 can be inductively and capacitively coupled with the processor 125 and/or the external powering system 145. The power source 130 can also be coupled with the valve 120. The power source 130 can be used, for example, to supply the processor with the power to send or receive information from the computing device 135. The power source 130 can be coupled with the valve 120 and be used to supply the power required to open or close the valve 120. The external powering system 145 can be connected to an AC outlet and/or utilize DC current from other sources.

The power source 130 can be rechargeable. The power source 130 can be configured to last for an approximate 1-36 months of usage. In some embodiments, the power source 130 is a battery that can be configured to receive an electric charge from an external powering system 145 via wireless recharging technology similar to what is currently available in other devices as Commercial Off The Shelf (COTS) application for wireless induction charging.

The external powering system 145 can comprise a charging pod. The charging pod can be plugged into an alternating current (AC) outlet. When placed in the proscribed location, such as on the front of the abdomen, the power source 130 in the catheter 105 can recharge through magnetic induction technology, for example.

In some embodiments, the computing device 135 can have a software which can be used to interpret the values sent from the sensor 115. In some embodiments, the sensor 115 is a pressure sensor and the computing device 135 can be used to alert a user about when their bladder is likely to contract and void. In some embodiments, the urine 155 amounts inside the bladder can be calibrated by feedback from the individual user after insertion or implantation. In some embodiments, the sensor can use other spectrums of energy, to include acoustics, to determine the fullness or volume of urine in the bladder. Different types of sensors can be embedded on the catheter to determine important metrics of bladder health including pH, volume, pressure, etc. In some embodiments, this can be accomplished through software that analyzes the sensor 115 response and utilizes machine learning algorithms to predict and interpret this data.

The sensor 115 device can utilize basic wireless transmission protocol to wirelessly send data to a computing device 135 with the control software on it. This can be accomplished in a manner similar to Bluetooth, 802.11 WiFi, SONAR, UltraSound, MedRadio or other wireless communications protocols.

In one embodiment, the sensor 115 can determine the pressure of urine 155 within the bladder 110 and send a signal to the processor 125. The processor 125 sends information on pressure level in the bladder 110 to the computing device 135. The computing device 135, using a software, determines whether urine 155 needs to be drained from the bladder 110. The computing device 135 will also notify the user to drain urine from the bladder. The user can actuate the valve 120 which will allow urine 155 to leave the bladder 110. In some embodiments, the sensor 115 can be used to determine when urine has been sufficiently drained from the bladder 110, such as by determining that the pressure level within the bladder 110 has dropped below a certain level. This information can be used to close the valve 120 and halt the flow of urine 155 from leaving the bladder 110. This sensing technology is not limited to pressure, and in some embodiments, other metrics can be used to make decisions with clinical impact.

The catheter 105 can be used to determine various conditions within the bladder 110. The sensor 115 can be a pH sensor, an ultrasonic sensor, a displacement sensor, acoustic sensor, etc. Different types and combinations of sensors can be used. For example, the catheter 105 can comprise a pH sensor and a pressure sensor.

The valve 120 can be configured to increase or decrease the flow rate of urine. For example, the valve can have varying degree of valve opening. The valve 120 opening can be configured to dilate and/or expand in order to increase the volumetric flow rate of urine leaving the bladder 110. For example, a pin valve can be used. This valve 120 can also be configured to be actuated by the pressure of urine 155 in the bladder 110.

As shown in FIG. 2, a bladder management system 200 can comprise a signal-generating sensor 205. In some embodiments, the bladder management system 200 can comprise a valve 210, an external actuator 230, the signal-generating sensor 205 within a catheter 215, and an external computing device 240. The signal generating sensor 205 can be an LC resonant sensor, an RFID device, or a speaker. In some embodiments, the system 200 can further comprise a microphone and/or an amplifier. The valve 210 can be configured to open and close using an external valve actuator 230. The external computing device 240 can be used to send and receive signals 225 to and from the signal-generating sensor 205. In some embodiments, the external computing device 240 can be programmed to interpret the signal 225 to indicate condition within a patient's bladder 220.

The user can use the external computing device 240 to generate a signal 225. The sensor 205 can receive the signal 225 from the external computing device 240 and generate a return signal 225 that can be analyzed and interpreted to determine metrics about the condition of the bladder and/or urine within the bladder (e.g. volume, pressure, pH level, etc.). The computing device 240 can display the desired information to the user or can be cataloged for further review and analysis. In some embodiments, this data may be used to send an alert or notify the user or caregiver based on either pre-determined settings or through machine learning algorithms and/or advanced data analysis techniques. For example, the computing device 240 can receive signal from the sensor 205 that can be interpreted to determine the volume of urine 235 in the bladder 220. Another example, an algorithm can be used to determine the pressure within the bladder 220 based on relationships with the volume of the bladder 220. Based on the information available or the notification provided, the user can manually open the valve 210 using the external actuator 230.

The sensor 205 can be configured to change its mechanical properties (e.g. color, size, shape, etc.) based on pressure changes inside the bladder 220. The user can use an external device to detect changes in mechanical properties of the sensor 205 by, for example, sending and/or receiving sound waves, light waves, etc. In some embodiments, the internal sensor 205 can function without a power source. By constructing the sensor 205 in a specific manner the external unit can observe changes in the resonant frequency characteristics.

The catheter 215 can comprise a computing device 240. For example, a computing device 240 can be coupled with the sensor 205 and use a software algorithm to determine urine 235 amount inside the bladder 220 based on data read from the sensor 205. The user can use an external device that can exchange information with the computing device 240 coupled with the sensor 205. In some embodiments, the computing device 240 can be linked to an external database. For example, an external database having patient data can be used with the computing device 240 to monitor the patient condition and manage bladder 220 by using data that has been collected and aggregated from other patients and sources. A database can catalog the dataset that will allow for analysis and algorithm development to improve accuracy and support predictive analytics.

Sensor

Figure 3:
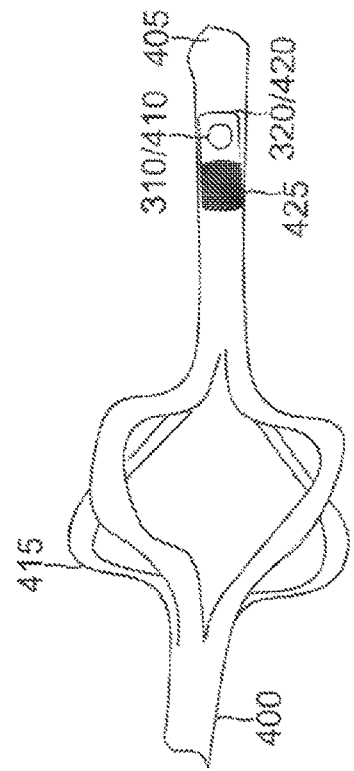
FIGS. 3 and 4 schematically show different embodiments of sensors used in the bladder management system.
Figure 4:
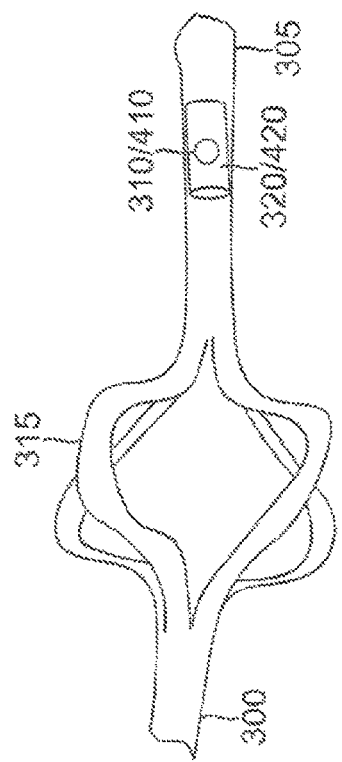

As schematically shown in FIGS. 3 and 4, sample embodiments of the device can comprise a catheter 300, 400 having a proximal end 305, 405. The catheter 300, 400 can comprise a lumen 310, 410 having a retaining portion 315, 415 near the proximal end 305, 405. The catheter 300, 400 can house a sensor 320, 420. As shown in FIG. 4, the sensor 420 can comprise a radio unit 425. For example, the radio unit 425 can be a transceiver. In some embodiments, the radio unit 425 can comprise a microphone. The radio unit 425 can be wirelessly coupled to the sensor 420 via different means, including inductive-capacitive coupling or energy transmission in other mediums such as SONAR, Ultra-Sound, Microwave, etc.

The retaining portion 315, 415 can be configured to transition from an expanded configuration as shown in FIGS. 3-4 to a collapsed configuration shown in FIG. 8A. The retaining portion 315, 415 can be a malecot anchor having a plurality of wings. In the expanded configuration, the retaining portion 315, 415 can retain and anchor the catheter 300, 400 within the bladder. In the collapsed configuration, the catheter can be received within and passed through the bladder neck and urethra without causing trauma to the urethra or significant modification to the human anatomy.

The catheter 300, 400 which includes the sensor 320, 420 can perform one or more of the following: measure important metrics of urine and the bladder; wirelessly relay this data to an external device; allow a mechanical valve to open upon user input; be semi-permanent, e.g. allowing long-term use and/or extended wear; be inserted via minimally invasive means; utilize wireless recharging or powering technology for the sensor 320, 420 or power storage unit; and be removed when the user wishes to remove the catheter.

Catheter

Figure 5:
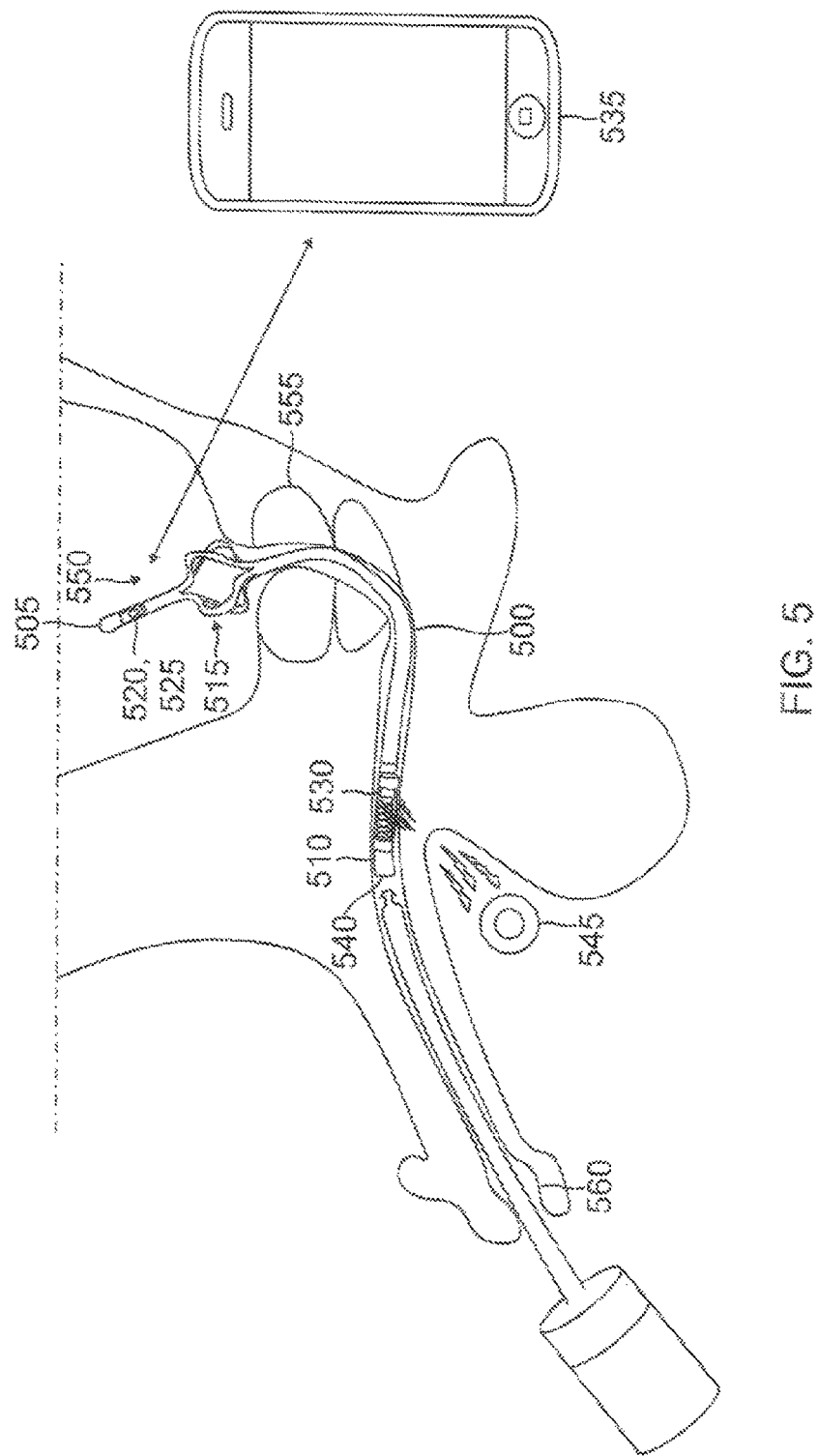
FIG. 5 shows a schematic drawing of a bladder management system used in a male urinary control system.

As shown in FIG. 5, the catheter 500 can be fully-internal, meaning the catheter 500 is not visible to the naked eye from the exterior, once the catheter 500 is inside the patient's body. The fully-internal catheter 500 can comprise a proximal portion 505 and a distal portion 510. The proximal portion 505 can comprise a retaining portion 515 and a sensor 520. The catheter 500 can comprise a lumen 525. The distal portion 510 can comprise a valve 530.

The sensor 520 can be placed proximal to the retaining portion 515. The sensor 520 can be configured to communicate with an external computing device 535. In some embodiments the computing device 535 is a mobile phone. In some embodiments, the external computing device 535 may be a transceiver that is able to receive and relay these signals to other devices. The valve 530 can comprise a mating structure 540. The mating structure 540 can be configured to mate with a corresponding structure of a catheter insertion device and/or that of an extraction device.

In some embodiments, the urine in the bladder 550 can be voided when the user utilizes an external actuator 545 to open the valve 530 and allows the urine to travel through the urethra 560. This signal can be controlled by the user through the use of an external computing device 535. In some embodiments, the valve 530 can comprise a magnetic ball valve, and the external actuator 545 car, comprise a magnet. In other embodiments, this external actuator 545 can be a combination of electronic control that may utilize an electromagnet to open the valve 530. As shown in FIG. 5, a user can place the external actuator 545 near the valve 530, e.g. on the skin of patient between the scrotum and the shaft of the penis, to open the valve 530. The valve 530 can be closed when the actuator 545 is away from the location of the valve 530 inside the patient's body. For example, the valve 530 can be closed when the actuator is inside a patient's side pocket.

Figure 7A:
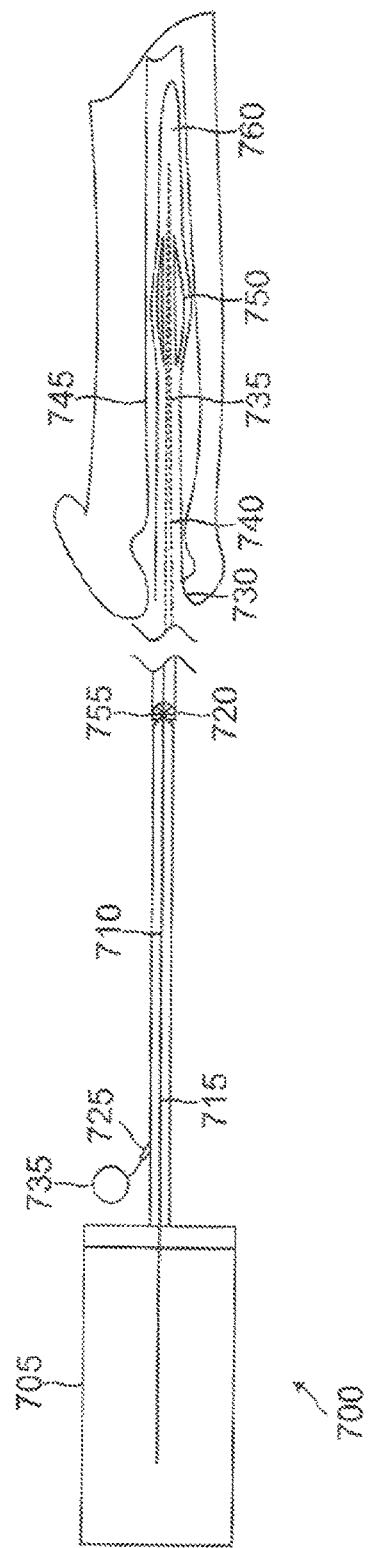
FIG. 7A shows a schematic drawing of an embodiment of an extraction device.
Figure 7B:
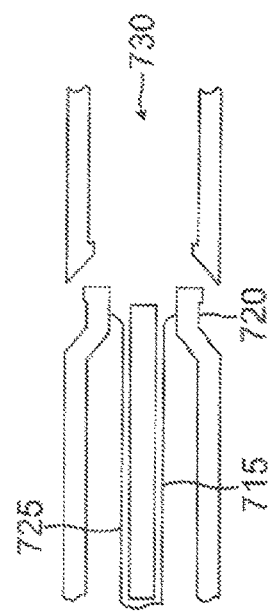
FIG. 7B shows a schematic drawing of an embodiment of a thruster tip of the extraction device of FIG. 7A.

The catheter 500 can be constructed in a shape and of a material that is conducive to entry utilizing a medical device, such as an insertion device 700 shown in FIGS. 7A and 7B, that will enter through the urinary tract. For example, the catheter 500 may be constructed of a material similar to other existing intermittent catheters on the market (such as PVC, Latex, Silicone, Polyurethane or any blend of these materials). In some embodiments, once inside the bladder 550, the catheter 500 can comprise a retaining portion 515 that can fix the catheter 500 to the wall of the bladder 550.

In some embodiments, the sensor 520 can be placed distal to the retaining portion 515. For example, the sensor 520 can be coupled to the valve 530. In some embodiments, the valve 530 can comprise an internal actuator. For example, the valve 530 can be configured such that an external computing device 535 can be used to open or close the valve 530 using a signal. In some embodiments, a valve 530 can be placed in the proximal portion 505 of the catheter. For example, the valve 530 can be placed on the neck of the bladder 550. In some embodiments, the catheter 500 can comprise a retaining portion 515 along a midsection or distal end of the body. For example, the catheter 500 can be configured such that the retaining portion 515 is placed on or near the prostate 555 or along the urethra 560 of the patient, instead of within the bladder 550 of the patient as shown. In some embodiments, this mechanism may be used in combination with the malecot anchor.

Valve

Figure 6A:
FIG. 6A shows a schematic drawing of an embodiment of the catheter portion of the bladder management system of FIG. 1.
Figure 6B:
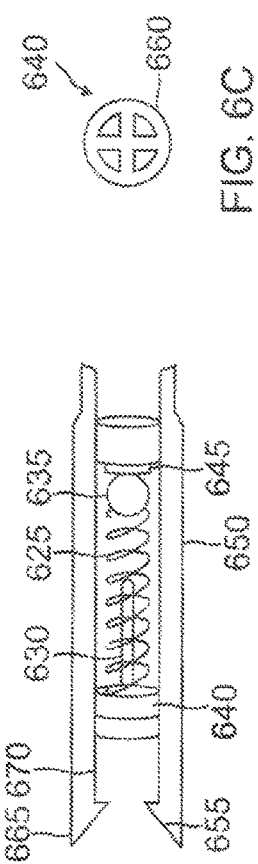
FIG. 6B shows an enlarged view of a valve portion of the catheter of FIG. 6A.

FIGS. 6A to 6D are detailed schematic drawings of the catheter 600 using a ball valve 605. As shown in FIG. 5A, the catheter 600 comprises an elongated midsection 610 between the proximal portion 615 and the distal portion 620. The elongated midsection 610 can comprise a flexible tube having a lumen. As shown in FIG. 6B, the valve 605 can be a cylindrical magnetic ball valve comprising a spring 625, a spring stabilizer 630, a magnetic ball 635, a distal seat 640, a proximal seat 645, and a mating structure 655. The proximal portion 615 can comprise a straight tip. In some embodiments, the proximal portion 615 comprises a coude tip.

Figure 6C:
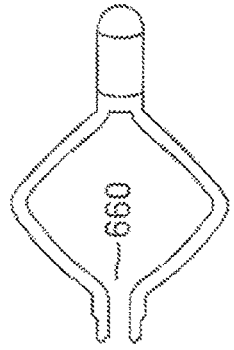
FIG. 6C shows a cross-section view of the valve portion of FIG. 6B across the line a-b.
Figure 6D:
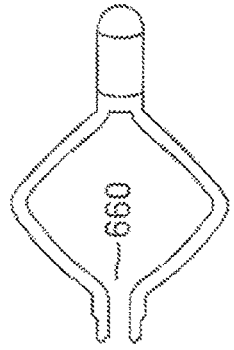
FIG. 6D shows an enlarged view of a retaining portion of the catheter of FIG. 6A.

The spring 625 can be coupled to the distal seat 640 and configured to constantly exert tension during opening and closing of the valve 605. The spring stabilizer 630 can be concentric to the center of the valve 605. The proximal seat 645 can be configured to trap the ball 635 (e.g. by having a ring shape with an inner radius smaller than the radius of the ball 635). The retainer 650 can be positioned distal and adjacent to the proximal seat 645. As shown in FIG. 6C, the distal seat 640 and the proximal seat 645 can comprise one or more inlets 660. The inlet 660 can be shaped and sized to pass a pushwire 715 shown and described below in reference to FIGS. 7A and 7B. As shown in FIG. 6D, the proximal portion 615 can comprise a fluid inlet 660. The proximal portion 615 can house a sensor. The mating structure 655 can comprise a tapered surface 665 and a ledge 670. The mating structure 655 can be configured to expand when thrusting a rigid corresponding structure, e.g. the thruster tip 825 of the extraction device 800 shown in FIG. 8. The mating structure 655 can comprise a magnetic material. In some embodiments, the mating structure 655 can comprise a conductive material that can be used to complete an external circuit and inform a user that the extraction device 800 is mated to the mating structure 830.

In some embodiments, the valve 605 can comprise a disc, plug, diaphragm, pinch, check, plunger, flap, duckbill, or other valve designed to actuate upon user input and/or at a calculated pressure threshold. In some embodiments, the valve 605 can comprise a manual squeeze valve (not shown) configured to manually open and close. The manual squeeze valve can comprise an elastic body in a closed state without manual adjustment. When the catheter 600 is inside the patient, the user may squeeze the valve 605 from the skin of the patient to open the valve 605. From squeezing the valve 605, the fluid inside the bladder can be drained.

User Insertion and Removal

A fully-internal catheter 600 can be used for extended periods and long-term use rather than requiring intermittent replacement as some existing catheter devices require. The long-term use of a fully-internal catheter 600 can aid in patient comfort, prevent and/or reduce psychological trauma from frequent replacement, reduce occurrence of urinary tract infections, etc. The catheter 600 device can be long-term use because it can be inserted and/or removed by utilizing medical devices, e.g. an insertion device 700, an extraction device 800, etc. The removal of the long-term use catheter 600 device can be in a similar manner as when the long-term use catheter 600 device is implanted within the patient. The insertion device 700 and the extraction device 800 can comprise structures corresponding to the mating structure 655 of the valve 605. The device has been designed in such a way that insertion and extraction can be completed by the user.

Insertion

As shown in FIG. 7A, the insertion device 700 can comprise a container 705, an insertion rod 710, a pushwire 715, a trigger 735, and one or more pull strings 725. The pushwire 715 can be a mandrel. As schematically shown in FIG. 7B, the insertion rod 710 further comprises a lip 720 connected to the one or more pull strings 725. The lip 720 can be configured to mate with the valve mating structure 830. For example, as shown in FIG. 7B, the lip 720 can comprise a bottleneck structure that mates with the ledge 845 of the mating structure 830. When prepared for insertion, the insertion device 700 will translate force along the axis of travel through the urethra 745 until the user chooses to disengage the mating mechanism. The lip 720 can be semi-rigid and have a stiffness sufficient to remain attached to the valve 755 mating structure 830 until disengaged by the user.

The container 705 can be in fluid communication with the rod 710. The container 705 can be configured to allow visual confirmation of material inside the container 705. For example, the container 705 can comprise a translucent material, such as translucent PVC. The rod 710 can comprise a hollow tube made of a medical grade material, such as nylon. The pushwire 715 can pass through the hollow tube of the rod 710 and the catheter 740 lumen and comprises a shape memory material used in similar medical applications. For example, the pushwire 715 can comprise a Teflon®-coated nitinol or stainless steel wire having a stiffness to allow bending and flexing without causing trauma to the urethra 745 while the catheter 740 is inserted inside the patient's body. The pushwire 715 can have a longitudinal length longer than the combined longitudinal length of the catheter 740 and the rod 710. As shown in FIG. 7A, the pushwire 715 has a length such that a portion of the pushwire 715 extends into the container 705, while the pushwire 715 extends fully along the erect length of the catheter 740 and the rod 710. During insertion, the pushwire 715 contacts the catheter tip 760 such that thrusting force from the pushwire 715 transports the catheter 740 along the urethra and to the bladder. In some embodiments, the trigger 735 can comprise a ring shape having a dimension to fit a human index finger. The trigger 735 can be connected to the pull string 725 which extends from the lip 720 and through an opening on the rod 710.

The insertion device 700 and the catheter 740 can be carried in a sterilized pouch. In some embodiments, the insertion device 700 and the catheter 740 can be in a mated state before use. In the mated state, the pushwire 715 extends through the valve 755 such that the valve 755 remains open to allow fluid flow. As shown in FIG. 7A, the retaining portion 750 of the catheter 740 can be folded in the mated state. A user may open the pouch comprising a catheter 740 and the insertion device 700 and insert the catheter 740 into the urethra. The user may move the catheter 740 by moving the catheter 740 proximally using the insertion device 700.

Once the retaining portion 750 reaches the bladder, the retaining portion 750 can expand as the user removes the pushwire 715 and allows the anchor to return to its resting state. The fluid within the bladder may drain from an opening 730 of the retaining portion 750 through the open valve 755, to the rod 710, and eventually to the container 705. The user may observe presence of fluid inside the container 705 to visually confirm placement of catheter 740 and that the catheter 740 has successfully reached the bladder. The user can then remove the pushwire 715 and allow the anchor to expand. The user can actuate the trigger 735 to collapse the lip 720 to disconnect the insertion device 700 from the catheter 740. The removal of the insertion device 700 can be done subsequent to visual confirmation of the placement of catheter 740. The user can move the insertion device 700 away from the catheter 740 while the catheter 740 remains within the patient's body.

In some embodiments, fluid flow through the valve 755 can be prevented before and after the insertion of the catheter 740. For example, the valve 755 can comprise an orifice completely sealed off by the pushwire 715 to prevent fluid flow. In some embodiments, the catheter 740 can comprise a sensor which can notify the user of fluid flow in the catheter 740 upon placing the retaining portion 750 inside the bladder.

Extraction Device

As shown in FIG. 8A, the extraction device 800 can comprise a handle 805, an extraction rod 810, a click button 815, and a visual indicator 820. The extraction rod 810 can comprise a cannula. As shown in FIG. 8B, the extraction device 800 can comprise a thruster 835 inside the extraction rod 810. The thruster 835 can comprise an extraction tip 825. The extraction tip 825 can be configured to mate with the mating structure 830 of the valve 755. For example, the extraction tip 825 can comprise a semi-rigid surface 860 that can be pushed past the tapered surface 855, and one or more latching wings 840 that can latch onto the ledge 850. The extraction tip 825 can comprise a magnetic material. In some embodiments, the extraction tip 825 can comprise a conducting material. The click button 815 can be located on the distal tip of the handle 805 opposite the extraction rod 810. The visual indicator 820 can be an LED light configured to actuator on or off when the extraction tip 825 abuts the valve mating structure 830. The visual indicator 820 can be located on the handle 805

The handle 805 can comprise an ergonomic structure and can house a spring. The click button 815 can be used to operate the thruster 835 from a protruding position and retracting position, having mechanics similar to a conventional retractable pen. The extraction device 800 can provide auditory and tactile notice to the user, such as when the click button is pressed, the button "clicks" to indicate that the thruster 835 position has changed. In some embodiments, the handle 805 and the extraction rod 810 can house electronic circuitry connected to the visual indicator. The electronic circuitry connected to the visual indicator 820 can remain broken until the conductive thruster tip 825 connected to the circuitry contacts the valve mating structure 830 to complete the circuitry. For example, the valve mating structure 830 can comprise an annular conductive surface, while the extraction tip 825 can comprise two or more disconnected probe ends configured to contact the annular conductive surface.

The extraction rod 810 of the extraction device 800 can be inserted in the urethra of a patient wearing the fully-internal catheter. The user can determine placement of the extraction tip 825 to the valve mating structure 830 by seeing the visual indicator light turn on. The extraction tip 825 and the valve mating structure 830 can magnetically attach. The user may push the click button 815 to push the latching wing 840 of the thruster tip 825 past the ledge 850. The thruster tip 825 can flex and collapse to push through the tapered surface 855 and contract to its original shape as the latching wing 840 moves past the ledge 850 to latch onto the ledge 850. The user may move the extraction device 800 to extract the catheter out of the patient's body and dispose the extraction device 800 and the catheter.

In some embodiments, the visual indicator 820 can remain on until the thruster tip 825 contacts the valve mating structure 830. In some embodiments, the visual indicator 820 can be located on the click button 815. Various different types of actuation mechanism can be used. For example, the thruster 835 can be actuated using a turn knob or a screw. In some embodiments, the click button 815 can be located on the side of the handle 805.

Figure 9:
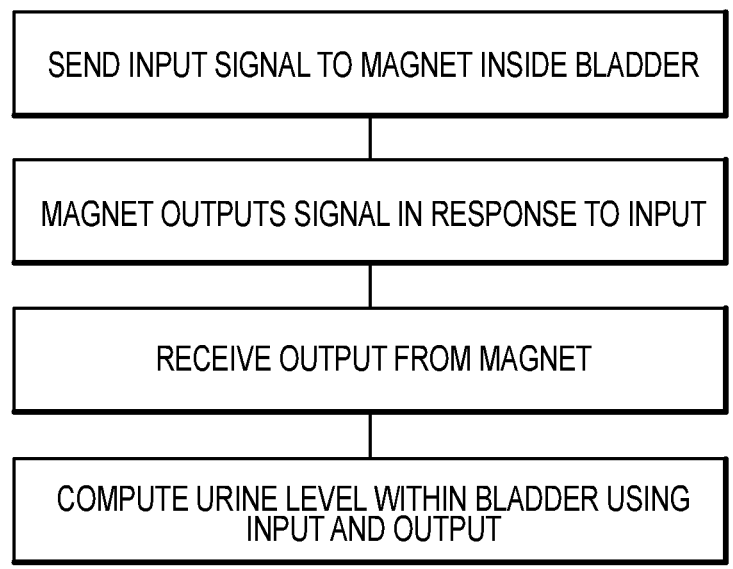
FIG. 9 is a functional block diagram which illustrates the operation of a sample sound sensor system.

FIG. 9 is a functional block diagram which illustrates the operation of a sample sound sensor system.

Among the many advantages of this invention include increasing the quality of life for individuals suffering from neurogenic bladder by: 1. reducing the risk of medical issues (urinary tract infections, false passage, etc.); 2. eliminating the need for indwelling or intermittent catheters and decreasing the number of catheters required for daily use (because of increased accuracy with which the user knows when catheterization is required); 3. allowing the user to control bladder voiding; 4. accommodating implanted, semi-permanent (useful life 3-6 months) device via minimally invasive means (via catheter); 5. minimizing problems from incontinence and related psychological impact (emotional trauma from accidental urinary voiding); and 6. transmits wireless report data similar to that done in urodynamic flow testing (pressure of bladder at different levels of fullness) more accurately and less invasively.

Although embodiments of the invention have been shown and described, it is to be understood that various modifications, substitutions, rearrangements and different parts, components, equipment, elements and/or process (method) steps, as well as other uses, of the wireless pressure sensor and valve for bladder can be made by those skilled in the art without departing from the novel spirit and scope of this invention.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5. Intel Core I & Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (N IC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein.

The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A device for bladder control management, the device comprising:
 a catheter having a proximal end and a distal end and configured to be implanted within a bladder of a patient, wherein a portion of the catheter comprises a lumen extending towards the proximal end and is configured to allow fluid to flow therethrough, the lumen being in fluid communication with an opening at the proximal end;
 a valve member in fluid communication with the lumen and opening;
 a retaining member positioned along a portion of the catheter adjacent to the proximal end, the retaining member configured to transition between an expanded configuration to retain the implantable catheter within the bladder and a collapsed configuration to allow the device to be received within and passed through a bladder neck and urethra;
 an insertion device configured to be connected to the catheter in order to properly position the catheter in a body and configured to be disconnected from the catheter when the catheter is properly positioned in the body, the insertion device comprising a container, wherein the container is configured to receive fluid from the lumen when the retaining member is in its expanded configuration; and an extraction device that is separate from the insertion device and that is configured to be connected to the distal end of the catheter when the catheter is in the body in order to pull the catheter out of the body;

wherein the insertion device comprises a second mating structure and the catheter comprises a first mating structure configured to mate with the second mating structure, wherein the second mating structure comprises a first configuration and a second configuration, and wherein the second mating structure expands to the first configuration in order to mate with the first mating structure.

2. The device of claim 1, wherein the distal end comprises an attachment mechanism configured to engage a corresponding attachment mechanism on a positioning/retrieval device for positioning and retrieving the device.

3. The device of claim 2, wherein upon disengagement of the corresponding attachment mechanisms from one another, fluid cannot flow into the insertion device.

4. The device of claim 1, wherein at least the catheter is comprised of a medical grade material.

5. The device of claim 1, wherein the second mating structure comprises a semi-rigid lip.

6. The device of claim 1, further comprising magnetics for operating the valve member.

7. The device of claim 1, further comprising at least one sensor.

8. The device of claim 7, further comprising a processor with wireless capability, wherein the processor is configured to communicate with the at least one sensor.

9. The device of claim 7, wherein the distal end comprises the first mating structure.

10. The device of claim 9, wherein the first mating structure comprises a tapered surface and a latching tip.

11. The device of claim 1, wherein the first mating structure comprises a first configuration and a second configuration, wherein the first mating structure is mated to the second mating structure when the first mating structure is in the first configuration.

12. The device of claim 1, wherein the first mating structure comprises a valve mating tip.

13. The device of claim 1, wherein the insertion device has a lip configured to be attached to a valve mating structure.

14. The device of claim 1, wherein the container is translucent.

15. The device of claim 1, wherein the extraction device comprises a handle.

16. The device of claim 1, wherein the extraction device comprises an extraction rod.

17. The device of claim 15, wherein the extraction device further comprises a click button on the handle, wherein the click button is configured to push a latching wing of a thruster tip.

* * * * *